(12) United States Patent
Bossmann et al.

(10) Patent No.: US 6,620,409 B2
(45) Date of Patent: Sep. 16, 2003

(54) HAIR AND SKIN CARE AGENTS

(75) Inventors: Britta Bossmann, Erkrath (DE); Ullrich Bernecker, Huertgenwald (DE); Detlef Hollenberg, Erkrath (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 10/178,177

(22) Filed: Jun. 24, 2002

(65) Prior Publication Data

US 2002/0182164 A1 Dec. 5, 2002

Related U.S. Application Data

(63) Continuation of application No. PCT/EP00/12817, filed on Dec. 15, 2000.

(30) Foreign Application Priority Data

Dec. 24, 1999 (DE) .......................... 199 62 877

(51) Int. Cl.[7] .................................. A61K 7/08
(52) U.S. Cl. ...................... 424/70.1; 424/401
(58) Field of Search ................. 424/401, 70.1

(56) References Cited

U.S. PATENT DOCUMENTS

| 5,198,209 | A | 3/1993 | Zhou et al. |
| 5,387,374 | A | 2/1995 | Westfechtel et al. |
| 5,945,093 | A | 8/1999 | Duvel |
| 6,482,418 | B1 * | 11/2002 | Loehl et al. ............ 424/401 |
| 2001/0006652 | A1 | 7/2001 | Kahre et al. |

FOREIGN PATENT DOCUMENTS

| DE | 197 10 154 | 9/1998 |
| WO | WO 92/22282 | 12/1992 |
| WO | WO 97/47281 | 12/1997 |
| WO | WO 99/11226 | 11/1999 |

\* cited by examiner

*Primary Examiner*—Jyothsan Venkat
(74) *Attorney, Agent, or Firm*—Stephen D. Harper; Gregory M. Mill; Glenn E. J. Murphy

(57) ABSTRACT

Cosmetic skin or hair compositions are provided comprising a combination of (A) a dialkyl carbonate of the formula $R^1OC(O)OR^2$ wherein $R^1$ and $R^2$ are a linear or branched $C_{6-22}$ alkyl group and (B) an aminoalkyl amide of the formula $R^3CONH(CH_2)_n$—$NR^4R^5$ wherein $R^3CO$ is a linear $C_{6-22}$ acyl group, $R^4$ and $R^5$ are selected from the group consisting of alkyl, hydroxyalkyl and aminoalkyl groups containing up to 6 carbon atoms or $R^4$ and $R^5$ together with the N atom form a 5- or 6-membered ring and n is a number from 2 to 6.

9 Claims, No Drawings

HAIR AND SKIN CARE AGENTS

CROSS-REFERENCE TO RELATED APPLICATIONS

This application is a continuation application under 35 U.S.C. §365(c) and under 35 U.S.C. §120 of International Application PCT/EP00/12817, filed Dec. 15, 2000 and under 35 U.S.C. §119 of German Patent Application No. 199 62 877.7 filed Dec. 24, 1999.

BACKGROUND OF THE INVENTION

This invention relates to cosmetic skin and hair care preparations containing a combination of a dialkyl carbonate and an aminoalkyl amide as active principles for improving the cosmetic properties of the keratin surface.

The function of many cosmetic preparations is to make the surface of the skin soft and smooth and the hair lustrous and easy to comb. This objective is generally achieved by the incorporation of various cosmetic oil components. Silicone oils have proved to be particularly effective and, accordingly, occupy a special position within the group of cosmetic oil components.

However, it is known that silicone oils, by virtue of their strong interfacial activity and spreading effect and their marked hydrophobia, not only are very easily absorbed by skin and hair, they are also difficult to remove completely from the keratin surface, for example by washing, with the result that they accumulate, for example build up on the hair, after repeated application. This spoils the cosmetic appearance and the effect of other treatments, for example coloring or permanent waving.

Accordingly, there has been no shortage of attempts to find active principles for improving the cosmetic properties of the keratin surface which do not have this unfavorable effect.

Dialkyl carbonates are known as cosmetic oil components, for example from WO 92/122282 A1. Their suitability for improving the feel and luster of the hair treated with them is described in DE 197 10 154 C2 and WO 97/47281 A1.

Aminoalkyl amides are known, for example, from U.S. Pat. No. 5,198,209 as cationic surfactants used in combination with silicones, anionic surfactants and N-alkyl-2-pyrrolidones as components in conditioning shampoos.

SUMMARY OF THE INVENTION

It has now surprisingly been found that not only do the conditioning properties of the two substances complement one another in the combination, the cosmetic properties of compositions containing the two components in effective quantities cannot be achieved by either of the two substances on their own. This applies in particular to the combability, feel and static charging of the hair treated with the compositions.

DETAILED DESCRIPTION OF THE INVENTION

Accordingly, the present invention relates to cosmetic skin or hair care compositions which contain a combination of active principles for improving the cosmetic properties of the keratin surface and which contain as active principles at least (A) a dialkyl carbonate with the formula $R^1OC(O)OR^2$, in which $R^1$ and $R^2$ independently of one another represent linear or branched $C_{6-22}$ alkyl groups, and at least (B) an aminoalkyl amide with the formula $R^3CONH(CH_2)_n$—$NR^4R^5$, in which $R^3CO$ is a linear $C_{6-22}$ acyl group, $R^4$ and $R^5$ independently of one another represent alkyl, hydroxyalkyl or aminoalkyl groups containing up to 6 carbon atoms or, together with the N atom, form a 5- or 6-membered ring and n is a number of 2 to 6.

Cosmetic compositions in the context of the present invention are any compositions and formulations which are suitable for applying the substances to the skin or to the hair. Suitable compositions of this type include, for example, water-free oils, gels, aerosols and stick preparations. However, they may also be water-containing preparations, for example emulsions or shaking mixtures (unstable emulsions), emulsion foams in the form of pump sprays or aerosols packs, emulsion sticks or emulsion gels.

In water-free preparations, the dialkyl carbonate (A) is preferably present in a quantity of 1 to 90% by weight while the aminoalkylamide (B) is preferably present in a quantity of 0.1 to 10% by weight. Water-free preparations may also contain other oil, fatty or wax components, solvents, propellent gases and perfumes.

The preparations according to the invention are preferably present in the form of an oil-in-water emulsion of which the oil phase contains the dialkyl carbonate (A).

The dialkyl carbonate (A) is preferably present in such emulsions in a quantity of 1 to 90% by weight, based on the oil phase, and more particularly in a quantity of 5 to 50% by weight, based on the oil phase.

The aminoalkyl amide (B) is preferably present in such emulsions in a quantity of 0.1 to 2 parts by weight per part by weight of the dialkyl carbonate. Since the aminoalkylamides are substantially insoluble in water, but contain a basic amino group capable of salt formation, they are present in the alkaline medium as a constituent of the oil component.

In a preferred embodiment, however, the compositions according to the invention contain an acid in a quantity which converts the aminoalkyl amide at least partly into a water-soluble salt. The aqueous phase of the composition should preferably assume a pH of 2 to 5 through addition of the acid.

Preferred acids are, for example, $C_{2-6}$ hydroxycarboxylic acids such as, for example, glycolic acid, lactic acid, malic acid, citric acid and tartaric acid. Other basically suitable acids are acetic acid, gluconic acid, ascorbic acid and inorganic acids such as, for example, phosphoric acid, sulfuric acid or hydrochloric acid.

Of the dialkyl carbonates with the formula $R^1$—O—C(O)—O—$R^2$, the symmetrical dialkyl carbonates where $R^1=R^2$ and which are obtainable by transesterification of low molecular weight dialkyl carbonates, for example diethyl carbonate, with $C_{6-22}$ alcohols are particularly suitable. A most particularly suitable product is, for example, di-n-octyl carbonate.

Other dialkyl carbonates with interesting performance properties contain branched alkyl groups. An industrially available product of this type is, for example, di-(2-hexyldecyl)-carbonate which is obtained by transesterification of diethyl carbonate with a Guerbet alcohol, 2-hexyl decanol, and which is occasionally referred to as "Guerbet carbonate".

The aminoalkyl amides are obtainable on an industrial scale by amide formation from $C_{6-22}$ fatty acids or esters thereof and N,N-disubstituted alkylenediamines with the formula $H_2N$—$(CH_2)_n$—$NR^4R^5$. The compounds are normally used as starting materials for the production of quaternary ammonium compounds or betaine surfactants. Dimethylaminopropyl stearamide and isostearamidopropyl morpholine are commercially available as Tego® Amid S18 (Tego Cosmetics) and Incrocromate® ISML (Croda Inc.), respectively. Other suitable aminoalkylamides are, for example, stearic acid dihydroxyethyl aminoethyl amide or myristic acid dimethyl aminopropyl amide.

Although, in principle, the compositions according to the invention can be processed with high-foaming surfactants to form emulsion-type hair shampoos and body washes, the preparations according to the invention are preferably used for the care, setting, coloring and lightening of the hair. Examples of such preparations are hair oils, hair gels, hair lotions, hair-conditioning creams and emulsions, hair treatments, hair setting emulsions and foams, coloring and lightening emulsions and permanent wave fixing lotions.

Besides the characteristic active-principle combinations, the preparations may contain the components typical of such products.

Optional components such as these are, for example, surface-active compounds, more particularly nonionic, ampholytic, zwitterionic and cationic surfactants. Suitable nonionic surfactants are, for example, products of the addition of ethylene oxide onto fatty compounds containing labile hydrogen atoms, for example onto fatty acids, fatty alcohols, fatty acid alkanolamides, fatty acid monoglycerides, sorbitan fatty acid esters, methyl glucoside fatty acid esters, castor oil, polypropylene glycols, propylene glycol monofatty acid esters and other fatty compounds. Other nonionic surfactants are the alkyl and/or alkenyl oligoglucosides, the fatty acid-N-alkyl glucamides, tri-(polyalkoxy)-alkyl phosphates and amine oxide surfactants. Suitable ampholytic surfactants are, for example, N-alkylaminocarboxylic acids; suitable zwitterionic surfactants are, for example, the betaine surfactants such as, for example, cocoalkyl dimethyl ammonium glycinate.

In another particularly preferred embodiment, the hair treatment preparations according to the invention additionally contain a surface-active quaternary ammonium, pyridinium or imidazolinium compound or a water-soluble cationic polymer in a quantity of 0.1 to 5% by weight, based on the composition.

Cationic surfactants of the quaternary ammonium, pyridinium or imidazolinium compound type are distinguished by the fact that one or two lipophilic alkyl or acyl groups containing 10 to 22 carbon atoms are attached to the nitrogen atom of a quaternary ammonium, pyridinium or imidazolinium structure. Typical examples of such quaternary ammonium surfactants are, for example, cetyl dimethyl benzyl ammonium chloride, lauryl trimethyl ammonium chloride, distearoyloxyethyl hydroxyethyl methyl ammonium chloride, cetyl pyridinium chloride or methyl-2-stearyl-3-stearoylamidoethyl imidazolinium methoxysulfate.

Suitable water-soluble cationic polymers are, for example, the copolymers of diallyl ammonium salts and acrylamides, quaternized vinyl pyrrolidine/vinyl imidazole polymers, condensation products of polyglycols and amines, polyethyleneimine, cationic silicone polymers, copolymers of adipic acid and dimethylaminohydroxypropyl diethylenetriamine, copolymers of acrylic acid and dimethyl diallyl ammonium chloride. Water-soluble cationic polymers such as these are commercially available, for example, under the names of Merquat® 550, Gafquat®, Luviquat® and Cartaretine®.

However, water-soluble derivatives of natural polymers, such as cellulose, starch, guar, chitin or proteins which are distinguished by recurring cationic groups in or on the polysaccharide or peptide chain, are also suitable. Products such as these are commercially available, for example, under the names of Polymer® JR400, Lamequat® L or Jaguar®.

Besides the dialkyl carbonate, the preparations according to the invention may also contain other oil components. Although silicone oils have the disadvantages mentioned above, their additional presence in the preparations according to the invention is not ruled out. This applies in particular to low-boiling cyclic silicones, such as cyclopentasiloxane for example. However, other oil and fatty components, particularly those which do not build up on the hair, even with frequent use, are preferred.

Suitable oil components are, for example, vegetable and animal or synthetic triglyceride oils, natural or synthetic wax esters, for example jojoba oil or cetyl palmitate, paraffin oils and synthetic hydrocarbons such as, for example, 1,3-dioctyl cyclohexane, squalane, fatty acid esters, such as isopropyl myristate, butyl stearate or n-hexyl laurate and other liquid esters.

Particularly suitable oil components which show excellent care properties in hair care products in conjunction with the combination of active principles according to the invention are dialkyl ethers containing 12 to 24 carbon atoms, more particularly symmetrical di-n-alkyl ethers. A particularly preferred oil component of this type is di-n-octyl ether which is commercially available as Cetiol® OE.

Finally, the preparations according to the invention may also contain other auxiliaries and additives including, for example, antimicrobial agents, deodorizing agents, preservatives, antidandruff agents, complexing agents, buffers, dyes, opacifiers, perfumes, solvents and cosmetic skin and hair care agents such as, for example, panthenol, vitamins, sebostatic agents, UV filters.

The following Examples are intended to illustrate the invention without limiting it in any way.

EXAMPLES

Hair care emulsions (hair rinses) with the following composition are prepared:

|  | 1 | 2 | C1 | C2 | C3 | C4 | C5 | C6 |
|---|---|---|---|---|---|---|---|---|
| (1) Lanette ® O | 2.7 | 2.7 | 2.7 | 2.7 | 2.7 | 2.7 | 2.7 | 2.7 |
| (2) Isopropyl myristate | 1.0 | 1.0 | 1.0 | 1.0 | 1.0 | 1.0 | 1.0 | 1.0 |
| (3) Cetiol ® OE | 0.75 | — | 0.75 | 0.75 | — | — | 0.75 | — |
| (4) Dioctyl carbonate | 0.75 | 0.75 | — | 0.75 | — | 0.75 | — | — |
| (5) Tego ® Amid S 18 | 0.8 | 0.8 | 0.8 | — | 0.8 | — | — | — |
| (6) Rewoquat ® W75 PG | 2.5 | 2.5 | 2.5 | 2.5 | 2.5 | 2.5 | 2.5 | 2.5 |
| (7) Dehyquart ® F 75 | 1.0 | 1.0 | 1.0 | 1.0 | 1.0 | 1.0 | 1.0 | 1.0 |

-continued

|  | 1 | 2 | C1 | C2 | C3 | C4 | C5 | C6 |
|---|---|---|---|---|---|---|---|---|
| (8) Phenoxyethanol | 0.4 | 0.4 | 0.4 | 0.4 | 0.4 | 0.4 | 0.4 | 0.4 |
| (9) PHB methyl ester | 0.2 | 0.2 | 0.2 | 0.2 | 0.2 | 0.2 | 0.2 | 0.2 |
| (10) Water | to 100 | to 100 | to 100 | to 100 | to 100 | to 100 | to 100 | to 100 |
| (11) Citric acid | 0.2 | 0.2 | 0.2 | 0.2 | 0.2 | 0.2 | 0.2 | 0.2 |
| (12) Panthenol | 0.15 | 0.15 | 0.15 | 0.15 | 0.15 | 0.15 | 0.15 | 0.15 |
| (13) Perfume | 0.3 | 0.3 | 0.3 | 0.3 | 0.3 | 0.3 | 0.3 | 0.3 |
| pH value |  |  |  |  | 2.6–4.5 |  |  |  |
| Wet combability | 1− | 1+ | 1− | 2− | 2− | 2 | 2+ | 3− |
| Feel (wet) | 1− | 1− | 1− | 2 | 2 | 1− | 1− | 2 |
| Dry combability | 1− | 1− | 2+ | 3 | 2− | 1− | 1− | 3 |
| Feel (dry) | 1 | 1 | 1 | 2− | 3 | 1 | 1 | 2 |
| Static charging | 1 | 1 | 2 | 1 | 1 | 2 | 2 | 1 |
| Build-up | None | None | None | None | None | None | None | None |

Commercial Products Used
Lanette® O: cetylstearyl alcohol (1:1)
Cetiol® OE : di-n-octyl ether
Tego Amid® S18: stearamidopropyl dimethylamine (stearic acid-N-(3-dimethylamino)-propylamide)
Rewoquat® W75PG: Quaternium-87, propylene glycol (methyl-2-norpalmalkyl-3-palm oil fatty acid amidoethyl imidazolinium methosulfate) (with 25% propylene glycol)
Dehyquart® F75: distearoylethyl hydroxyethyl methyl ammonium methosulfate (containing 25% cetyl/stearyl alcohol)

Preparation

Constituents (1) to (9) of the oil phase were heated to 80° C. and mixed in a mixing vessel.

The citric acid was dissolved in water and the solution was heated to 80° C. The oil phase was emulsified into the heated water phase while stirring. After cooling of the mixture to 35° C., panthenol and perfume oil were added and mixed in by stirring.

Performance Tests

1. Determination of wet combability 1.1 Pretreatment of the hair tresses

Dry hair tresses weighing ca. 2 g (Fischbach and Miller, Type 6923) were blonded once for 30 minutes with 32 g of blonding mixture (commercial product Poly Blond Normal Aufheller). After the blonding mixture had been washed out, the hair tresses were directly subjected, i.e. without drying, to permanent waving with the commercial product Poly Lock Normal. The contact times of the wave component and the fixing component were 30 and 15 minutes, respectively. After the fixing component had been rinsed out, the tresses were dried and conditioned for at least two days under ambient conditions.

1.2 Determination of wet combability

Before the determination, the rinsed hair tresses were intensively shampooed with 0.2 ml of a 50% aqueous solution of Texapon® N25 (28% solution of sodium lauryl ether sulfate in water) and then rinsed. 1 g of the preparation to be tested was then uniformly massaged into the hair. Rinse-off products were left on the hair for 1 minute and then carefully rinsed out. After massaging (in the case of leave-on products) or after rinsing (in the case of rinse-off products), the hair was combed with a fine-tooth hard rubber comb and the combing resistance was subjectively evaluated. Comparison preparations were then tested in the same way on the same tress. Evaluation was based on a scale of 1 (=very good) to 5 (=very poor).

The results are set out in Table.

2. Determination of dry combability

The determination was carried out as described in 1.2 except that, before the determination, the hair was dried for 2 hours in a warm air stream (30° C., 20% rel. humidity) and conditioned for 12 hours at 30° C./20% rel. humidity.

3. Determination of electrostatic charging

Electrostatic charging was investigated as the same time as dry combability with electrostatic charging allowed. To this end, the hair tresses were combed 20 times for 10 secs. with a fine-tooth hard rubber comb and the spreading apart of the hair tresses caused by static charging was evaluated.

Evaluation was carried out by scoring on a scale of 1 (very little) to 3 (high charging).

4. Feel evaluation

The feel of the wet and dry hair was evaluated by manual sensory testing and evaluation on a scale of 1 (very soft) to 5 (straggly).

5. Build-up

Build-up was evaluated on non-pretreated but shampooed (as in 1.2) and dried (as in 2.) hair tresses by manual sensory testing for residues.

What is claimed:

1. A cosmetic skin or hair care composition comprising a combination of (A) a dialkyl carbonate selected from the grouod consisting of di-n-octyl carbonate and di-(2-hexvyldecyl)-carbonate , (B) an aminoalkyl amide selected from the group consisting of dimethylaminopropyl stearamide, isostearamidopropyl morpholine, stearic acid dihydroxyethyl aminoethyl amide and myristic acid dimethyl aminopropyl amide.

2. The composition of claim 1 wherein the composition is present in the form of an oil-in-water emulsion of which the oil phase contains the dialkyl carbonate (A).

3. The composition of claim 2 wherein the dialkyl carbonate (A) is present in a quantity of 1 to 90% by weight, based on the oil phase.

4. The composition of claim 3 wherein the dialkyl carbonate is present in a quantity of 5–50% by weight, based on the oil phase.

5. The composition of claim 3 wherein the arninoalkyl amide (B) is present in a quantity of 0.1 to 2 parts by weight per part by weight of the dialkyl carbonate.

6. The composition of claim 1 wherein is an acid present in a sufficient quantity to give the aqueous phase of the composition a pH value of 2 to 5.

7. The composition of claim 6 wherein the acid is a C6–22 hydroxycarboxylic acid.

8. The composition of claim 1 wherein a surface-active quaternary ammonium, pyridinium or imidazolium compound or a water-soluble cationic polymer is additionally present in a quantity of 0.1 to 5% by weight.

9. A method for improving the cosmetic properties of the keratin surface which comprises applying to the skin or hair a composition comprising a combination of (A) a dialkyl carbonate selected from the group consisting of di-n-octyl carbonate and di(2-hexyldecyl)-carbonate, and (B) an aminoalkyl amide selected from the group consisting of dimethylaminonpropyl stearamide, isostearamidopropyl morpholine, stearic acid dihydroxyethyl aminoethyl amide and myristic acid dimethyl aminopropyl amide.

* * * * *

UNITED STATES PATENT AND TRADEMARK OFFICE
CERTIFICATE OF CORRECTION

PATENT NO. : 6,620,409 B2
DATED : September 16, 2003
INVENTOR(S) : Bossmann et al.

It is certified that error appears in the above-identified patent and that said Letters Patent is hereby corrected as shown below:

Column 6,
Line 41, delete "grouod", and insert therefore -- group --.
Line 42, delete "hexvyldecyl)", and insert therefore -- hexyldecyl) --
Line 56, delete "arninoalkyl", and insert therefore -- aminoalkyl --
Line 59, after "wherein", delete "is" and after "acid", insert -- is --

Column 8,
Line 1, delete "ethylaminonpropyl" and insert therefore -- ethylaminopropyl --

Signed and Sealed this

Twenty-third Day of November, 2004

JON W. DUDAS
*Director of the United States Patent and Trademark Office*